United States Patent [19]

Imran

[11] Patent Number: 5,409,000
[45] Date of Patent: Apr. 25, 1995

[54] ENDOCARDIAL MAPPING AND ABLATION SYSTEM UTILIZING SEPARATELY CONTROLLED STEERABLE ABLATION CATHETER WITH ULTRASONIC IMAGING CAPABILITIES AND METHOD

[75] Inventor: Mir A. Imran, Palo Alto, Calif.

[73] Assignee: Cardiac Pathways Corporation, Sunnyvale, Calif.

[21] Appl. No.: 121,166

[22] Filed: Sep. 14, 1993

[51] Int. Cl.⁶ .................... A61B 5/04; A61N 1/05
[52] U.S. Cl. .................. 128/642; 128/660.03; 128/662.06; 607/122; 607/123
[58] Field of Search .......... 128/642, 660.03, 662.06; 607/119, 122, 123, 125, 126, 128

[56] References Cited

U.S. PATENT DOCUMENTS

| | | | |
|---|---|---|---|
| 4,582,061 | 4/1986 | Fry | 128/660.01 |
| 4,706,681 | 11/1987 | Breyer et al. | 128/642 |
| 4,794,931 | 1/1989 | Yock | 128/662.06 |
| 5,029,588 | 7/1992 | Yock et al. | 128/660.03 |
| 5,054,492 | 10/1991 | Scribner et al. | 128/662.06 |
| 5,156,151 | 10/1992 | Imran | 128/642 |
| 5,228,442 | 7/1993 | Imran | 607/122 |
| 5,255,679 | 10/1993 | Imran | 607/122 |
| 5,263,493 | 11/1993 | Avitall | 607/122 |
| 5,295,484 | 3/1994 | Marcus et al. | 128/660.03 |
| 5,324,284 | 6/1994 | Imran | 607/122 |
| 5,327,889 | 7/1994 | Imran | 607/122 |

FOREIGN PATENT DOCUMENTS 2504394 10/1982 France ............ 128/642

Primary Examiner—Krista M. Pfaffle
Attorney, Agent, or Firm—Flehr, Hohbach, Test, Albritton & Herbert

[57] ABSTRACT

Endocardial mapping and ablation system for introduction into a chamber of the heart formed by a wall and having a passage leading thereto comprising a catheter probe having a distal extremity adapted to be positioned in the chamber of the heart. The catheter probe is comprised of a plurality of flexible longitudinally extending circumferentially spaced-apart arms adapted to be disposed within the chamber of the heart. Electrodes are carried by the arms and are adapted to be moved into engagement with the wall of the heart. Markers visibly ultrasonically are carried by the arms for encoding the arms so that the one arm can be distinguished from another. An ablation catheter is carried by and is slidably mounted in the catheter probe and has a distal extremity movable into the chamber of the heart while the catheter probe is disposed therein. The ablation catheter has control means whereby the distal extremity can be moved independently of movement of the catheter probe while the distal extremity of the catheter probe is in the chamber of the heart. An ablation electrode is carried by the distal extremity of the ablation catheter. Ultrasonic viewing means is carried by the distal extremity of the ablation catheter. The distal extremity of the ablation catheter is movable into positions to view ultrasonically the markers carried by the arms of the catheter probe so that the arms can be identified and the spacing of the arms can be ascertained.

7 Claims, 2 Drawing Sheets

ENDOCARDIAL MAPPING AND ABLATION SYSTEM UTILIZING SEPARATELY CONTROLLED STEERABLE ABLATION CATHETER WITH ULTRASONIC IMAGING CAPABILITIES AND METHOD

This invention relates to an endocardial mapping and ablation system utilizing a separately controlled steerable ablation catheter with ultrasonic imaging capabilities and method.

In U.S. Pat. No. 5,156,151 there is disclosed an endocardial mapping and ablation catheter with circumferentially spaced apart electrodes carried by a plurality of longitudinally extending circumferentially spaced-apart arms. In such a catheter, it has been found that it is important after the arms have been deployed in a chamber of the heart to ascertain the locations of the arms to ascertain whether or not the arms are equally spaced apart and if not the spacing between the arms so that corrections can be made in the mapping calculations to account for the various spacings between the arms. In addition in connection with such mapping and ablation operations it is important to be able to visualize the portion of the wall forming the chamber of the heart which is to be ablated during the procedure to be sure that ablation is not taking place in an inappropriate location, as for example at a valve.

In the U.S. Pat. No. 4,794,931 there has been disclosed a catheter apparatus and system which can be utilized for ultrasonic imaging. However, there is no disclosure to how such an apparatus and system can be utilized in conjunction with an endocardial mapping and ablation catheter to achieve the desired ultrasonic imaging capabilities. There is therefore a need for an endocardial mapping and ablation system which provides the desired capabilities.

In general, it is an object of the present invention to provide an endocardial mapping and ablation system utilizing a separately controlled steerable ablation catheter with ultrasonic imaging capabilities and a method which makes possible various diagnostic and therapeutic procedures.

Another object of the invention is to provide a system, catheter and method of the above character which makes it possible to ascertain the location of the arms after they have been deployed in a chamber of the heart.

Another object of the invention is to provide a system, catheter and method which makes it possible to achieve accurate results while still having the arms positioned with different spacings between each other.

Another object of the invention is to provide a catheter and method of the above character in which it is possible to view the area to be ablated prior to ablation to ensure that ablation is being carried out in the appropriate location.

Another object of the invention is to provide a catheter and method of the above character which makes it possible to ascertain when the myocardium has been contacted.

Another object of the invention is to provide a catheter and method of the above character which makes it possible to ascertain the depth of a lesion formed by the ablation catheter.

Additional objects and features of the invention will appear from the following description in which the preferred embodiments are set forth in detail in conjunction with the accompanying drawings.

In general, the endocardial mapping and ablation system incorporating the present invention is for introduction into a chamber of the heart formed by a wall and having a passage leading thereto. A catheter probe is provided having a distal extremity which is provided with a plurality of longitudinally extending circumferentially spaced-apart arms. The arms carry a plurality of electrodes adapted to face the wall forming the chamber of the heart. An ablation catheter is carried by and is slidably mounted in the catheter probe and has a distal extremity movable into the chamber of the heart in which the catheter probe is disposed. The ablation catheter has control means whereby the distal extremity of the ablation catheter can be moved independently of movement of the catheter probe while the distal extremity of the catheter probe is disposed in the chamber. The ablation catheter has an ablation electrode mounted on the distal extremity. Ultrasonic viewing means is carried by the distal extremity of the ablation catheter. The arms of the catheter probe having markers encoding said arms. The markers are visible ultrasonically whereby specific arms can be identified ultrasonically and the spacing between the arms can be ascertained. The ultrasonic viewing capabilities of the ablation catheter also makes it possible to view the location in the wall where an ablation is to be performed to ensure that the ablation catheter is in contact with the wall of the heart.

Figure 1:
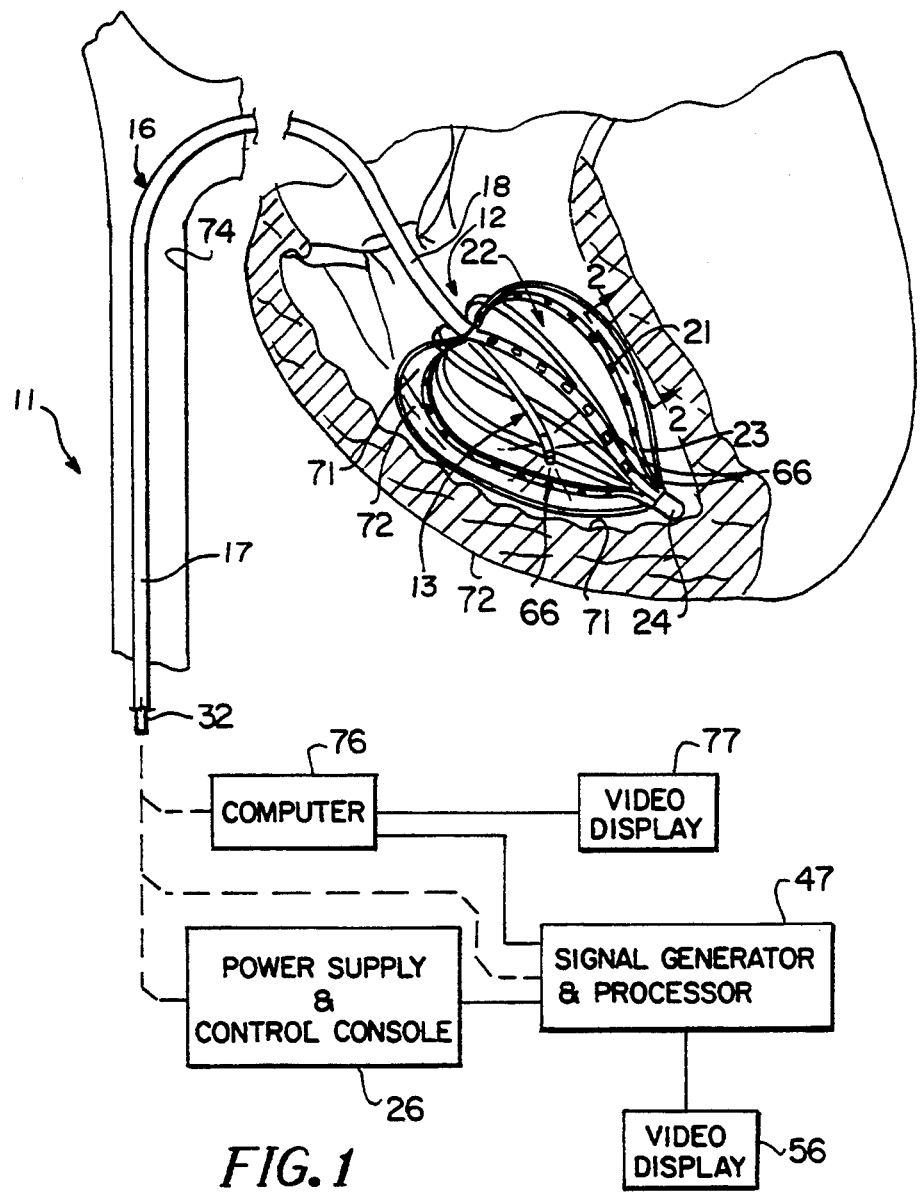
FIG. 1 is a schematic illustration showing the use of an endocardial mapping and ablation system utilizing a separately controlled ablation catheter with ultrasonic imaging capabilities deployed in a chamber of the heart to be used for mapping and ablation.

More in particular, the endocardial mapping and ablation system 11 utilizing a separately controlled steerable ablation catheter with ultrasonic imaging capabilities is shown in FIG. 1. It consists of a catheter probe 12 and an ablation catheter 13 carried thereby and slidably mounted therein. The catheter probe 12 is described in detail in the U.S. Pat. No. 5,156,151 and also in application Ser. No. 07/894,529, filed on Jun. 5, 1992, now U.S. Pat. No. 5,324,284. As described therein it is comprised of a flexible elongate member 16 formed of a suitable material such as plastic which is provided with proximal and distal extremities 17 and 18. The catheter probe 12 can be provided with a plurality of lumens (not shown) extending from the proximal extremity 17 to the distal extremity 18 as shown in application Ser. No. 07/894,529, filed on Jun. 5, 1992, now U.S. Pat. No 5,324,284.

The catheter probe 12 is also provided with a plurality of longitudinally and radially spaced-apart electrodes 21. Expandable means 22 is provided for carrying the electrodes 21 and as shown is formed of a plurality of longitudinally extending arms 23, the proximal extremities of which are secured to the distal extremity of the flexible elongate member 16 and the distal extremities of which are secured together in a cylindrical tip 24. Various means can be provided (not shown) for moving the arms between contracted and expanded positions. For example, pull wires such as disclosed in the application Ser. No. 07/894,529, filed on Jun. 5, 1992, now U.S. Pat. No. 5,324,284, can be utilized or alternatively the arms can be formed with a shape memory material as disclosed in application Ser. No. 08/044,255, filed Apr. 7, 1993 which can be energized and de-energized to provide movement between contracted and expanded positions. The electrodes 21 are connected by conductors extending into the arms 23 and through one or more lumens of the flexible elongate member 16 to the proximal extremity 17 and thence to the power supply and control console 26 where mapping procedures can be carried out.

Figure 4:
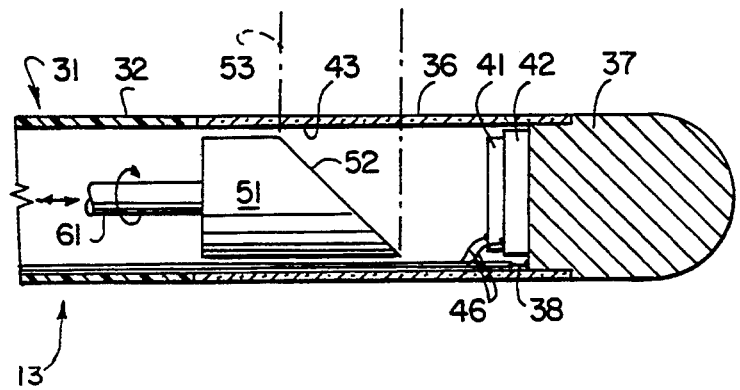
FIG. 4 is an enlarged cross-sectional view of the distal extremity of the separately controlled steerable ablation catheter with ultrasonic imaging capabilities incorporating the present invention.

The ablation catheter 13 is a separate device slidably mounted in a lumen (not shown) of the flexible elongate member 16. As shown in FIG. 4, the ablation catheter 13 consists of a flexible elongate member 31 formed of a suitable material such as a medical grade plastic and provided with a plurality of lumens as described in patent application, Ser. No. 07/894,529, filed on Jun. 5, 1992, now U.S. Pat. No. 5,324,284. A cylindrical tip 36 is provided on the distal extremity 32 of the flexible elongate member 31 and typically is formed of a material which is transparent to ultrasonic energy for purposes hereinafter described. The tip 36 is secured to the distal extremity 32 by a suitable means such as an adhesive. The distal extremity of the cylindrical tip 36 is closed off by a hemispherical tip 37 formed of a suitable conductive material such as platinum and which is bonded to the distal extremity of the cylindrical tip member 36. A conductor 38 is bonded to the tip 37 and extends to the proximal extremity of the flexible elongate member 31 and is connected to the power supply and control console 26 so that RF energy to be used for ablation can be supplied to the tip 37 when desired.

Means (not shown) is provided for steering the distal extremity 33 of the flexible elongate member 31 and can be of the type described in application, Ser. No. 07/894,529, filed on Jun. 5, 1992, now U.S. Pat. No. 5,324,284. The distal extremity of the ablation catheter 13 is provided with ultrasonic imaging capabilities which takes the form of an ultrasonic transducer 41 of a conventional type which is secured to a support member 42 mounted within a cavity 43 of the cylindrical tip member 36. The support member 42 is mounted in the fixed position immediately proximal of the tip 37 in such a manner so that the ultrasonic transducer 41 extends at an angle which is substantially perpendicular to the axis of the cylindrical tip member 36. Conductors 46 are connected to the front and rear sides of the ultrasonic transducer 41 and extend through lumens (not shown) to the proximal extremity of the flexible elongate member 31 and are connected to the signal generator and processor 47.

A member 51 is disposed within the cavity 43 immediately proximal of the transducer 41 and is formed of a material such as a reflecting metal which is capable of reflecting ultrasonic energy and is usually provided with an inclined surface that is inclined at a suitable angle, as for example 45° so that it is able to reflect and receive ultrasonic energy at a 45° angle with respect to the longitudinal axis of the cavity 43. Thus the inclined surface 52 on the member 51 which is circular in cross-section reflects an oval-shaped beam 53 through the wall of the cylindrical tip member 36 in a direction which is substantially perpendicular to the axis of the cylindrical member 51. The cylindrical member 51 can remain stationary permitting a different angle of view to be achieved by steering the distal extremity 33 of the flexible elongate member 31 and viewing the reflected ultrasonic energy or echoes by the surface 52 which directs them to the transducer 41 that converts them to electrical energy. This electrical energy in the form of electrical signals is transmitted through the wires 46 to the signal generator and processor 47 which supplies the information to a video display 56.

Alternatively, the cylindrical member 51 can be secured to a flexible cable 61 which can extend to the proximal extremity of the flexible elongate member 31 where it can be attached to a handle (not shown) and rotated manually. In addition the cylindrical member 51 can be moved longitudinally with respect to the tip member 36 toward and away from the transducer 41 to provide viewing of a larger region surrounding and extending longitudinally of the tip member 36. Alternatively the flexible cable 61 can be connected to a motor (not shown) also provided in the handle as described in U.S. Pat. No. 4,794,931 so that the ultrasonic signals are directed outwardly and received inwardly relative to the longitudinal axis of rotation of the rotatable element 51 to thereby permit rapid and substantially continuous viewing of the region surrounding the distal extremity of the ablation catheter.

Figure 2:
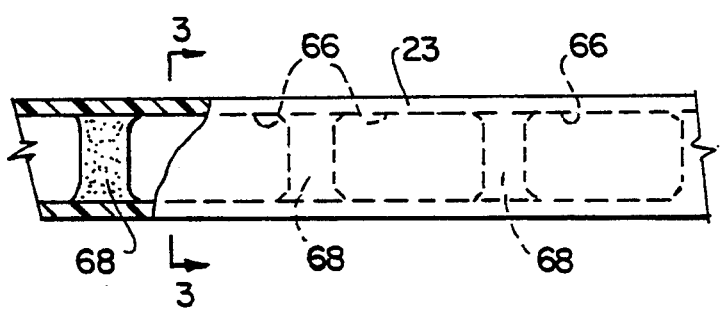
FIG. 2 is a view of one of the arms shown in FIG. 1 looking along the line 2—2 of FIG. 1.
Figure 3:
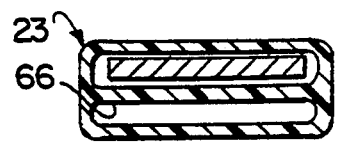
FIG. 3 is a cross-sectional view taken along the line 3—3 of FIG. 2.

In order to enhance the usefulness of the ablation catheter 13 in conjunction with the catheter probe 12, the arms 23 of the catheter probe 12 are encoded with markers 66 (see FIGS. 2 and 3) which are visible to ultrasonic energy. Such markers 66 have been provided in the form of encapsulated air bubbles. Thus, by way of example, one of the markers 66 can be placed on one of the arms 23, two markers 66 on the second arm, three markers 66 on the third arm, four markers 66 on the fourth arm as shown in FIG. 2, and so forth so that each of the arms can be identified when viewed ultrasonically. Such air bubbles 66 can be formed in an arm 23 by providing a lumen 67 extending longitudinally of the arm 23 and providing walls or barriers 68 of a suitable epoxy at spaced intervals and inflating the chamber forming the bubble 66 by introducing air by a syringe (not shown) penetrating the wall or barrier 68. The syringe can then be withdrawn and another barrier is formed which thereafter is penetrated by the syringe to provide another bubble 66. This procedure is continued until the desired number of bubbles have been provided to encode that arm. The other arms are encoded in a similar manner.

Operation and use of the endocardial mapping and ablation system in conjunction with the separately controlled steerable ablation catheter in performing the method of the present invention may now be briefly described as follows. The method for introducing the catheter probe 12 is described in U.S. Pat. No. 5,156,161 and as described therein can be introduced through the superior or inferior vena cava into the right atrium and then advanced into the right ventricle 71 which is in one of the chambers of the heart 72 formed by a wall 73 which has a passage 74 leading thereto as hereinafter described of a patient under examination. The catheter probe 12 is operated to cause the expandable means 22 to expand from a contracted position and move the arms 23 and the electrodes 21 carried thereby into engagement with the wall 73 of the heart 72 as shown particularly in FIG. 1.

As described in application, Ser. No. 07/894,529, filed on Jun. 5, 1992, now U.S. Pat. No. 5,324,284, the various potentials which are detected by the electrodes 21 are supplied to a computer (not shown) to form an isochronal map which can be displayed on a computer screen (not shown). The computer in making computations for making the isochronal map generally assumes that the arms are spaced-apart equally in a circumferential direction. It has been found that this is not necessarily the case because of abnormalities in the wall of the heart forming the chamber in which the probe is disposed and for other reasons. In order to provide a more accurate isochronal map, it is therefore desirable that the spacing between the various arms be ascertained. This can be accomplished by appropriately positioning the distal extremity 33 of the ablation catheter 13. The ablation catheter 13 can be inserted into the chamber of the heart at the same time the catheter probe 12 is inserted or if desired it can be inserted after the catheter probe 12 has been positioned in the chamber 71. In either event, the ablation catheter 13 has its distal extremity 33 moved into a position in which the arms 23 can be viewed interiorly and the markers 66 carried by the interior surfaces of the arms 23 can be viewed.

This ultrasonic viewing makes it possible to ascertain the spacing between the various arms and also to identify the arms. This information is supplied to the signal generator and processor 47 and to the video display 56 as well as to the computer 76 so that it can be utilized for making corrections in the computations with respect to the spacing between the arms to provide a more accurate isochronal map of the potentials being mapped. As pointed out previously, this ultrasonic imaging can be achieved by manually moving the distal extremity 33 of the ablation catheter 13 to obtain the desired ultrasonic viewing. Alternatively, the cylindrical member 51 can be rotated manually or advanced longitudinally manually. Also, alternatively the cylindrical member 51 can be rotated by motor means.

In addition to utilizing the ablation catheter 13 for ascertaining the locations of the arms 23, the ablation catheter 13 can be utilized for viewing the area of the wall 73 in which an ablation is to be performed to ascertain whether or not the site for the ablation is appropriate and to be sure that critical parts of the heart within the chamber, as for example a valve will not be ablated. To accomplish this, the distal extremity 33 of the ablation catheter 13 is moved into engagement with the wall with the tip 37 engaging the wall. The side viewing ultrasonic capabilities of the distal extremity 33 of the ablation catheter 13 can be utilized to view that region immediately prior to ablation being performed to be sure that the distal extremity of the ablation catheter is appropriately positioned. If not, the catheter can be moved until it is in the proper position. In this manner it is possible with the system and method of the present invention to ensure that the ablation will occur in the proper location and that critical parts of the heart, as for example valve apparatus will not be damaged.

Figure 5:
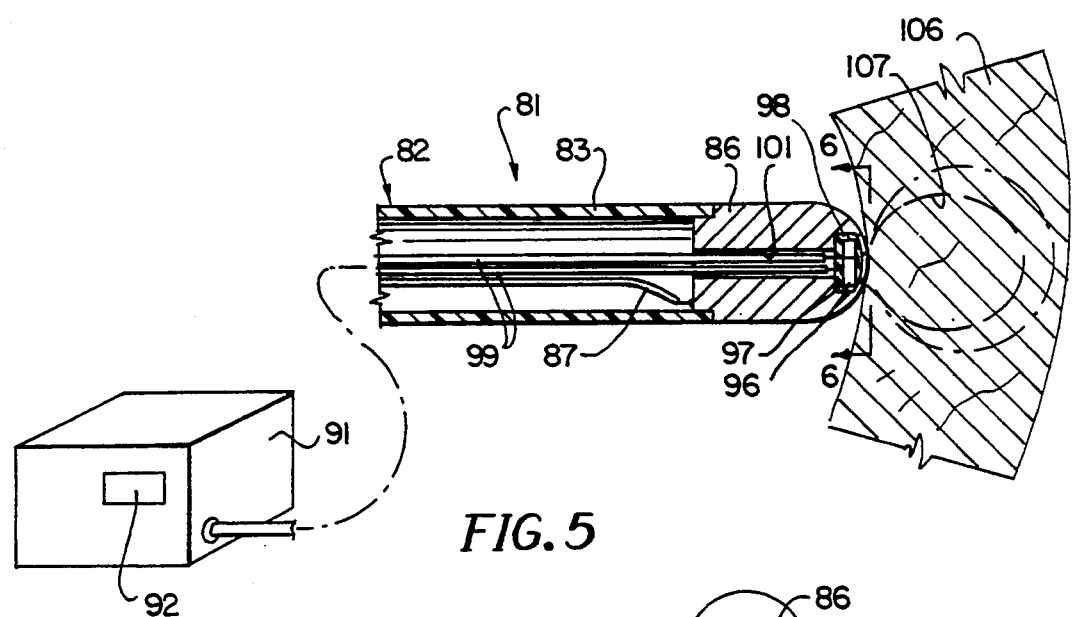
FIG. 5 is a cross-sectional view of another embodiment of an ablation catheter incorporating the present invention having forward looking ultrasonic capabilities.
Figure 6:
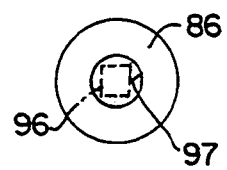
FIG. 6 is a view looking along the line 6—6 of FIG. 5.

Another embodiment of a separately controlled steerable ablation catheter 81 is shown in FIGS. 5 and 6, and as shown therein consists of a flexible elongate tubular member 82 of which only the distal extremity 83 is shown, which can be constructed in the manner disclosed in application U.S. Ser. No. 07/983,732, filed on Dec. 1, 1992, now U.S. Pat. No. 5,348,554. An ablation tip 86 formed of a suitable material such as platinum and having a hemispherical extremity as shown is secured to the distal extremity 83. It is connected to a conductor 87 which extends through the flexible elongate tubular member 82 to the proximal extremity (not shown) and thence to a control console 91 of the type described in application Ser. No. 07/983,732 filed on Dec. 1, 1992, now U.S. Pat. No. 5,348,554. Means (not shown) can be provided for steering the distal extremity as disclosed in said application. Also, means can be provided for cooling the ablation tip 86 in the manner described in application Ser. No. 07/983,732, filed on Dec. 1, 1992, now U.S. Pat. No. 5,348,554.

The catheter 81 is provided with forward looking ultrasonic capabilities and is provided with an ultrasonic transducer 96 that is mounted within a circular recess 97 extending inwardly of the tip 86. The ultrasonic transducer 96 is coated with an appropriate insulating material, as for example a hydrogel, which in addition to isolating the same from the tip 86 also serves to provide a good impedance match between the transducer 96 and the medium in which the catheter 81 is disposed, as for example in blood. The front and back sides of the ultrasonic transducer 96 are connected to conductors 99 which extend from the transducer through a bore 101 in the tip electrode 86 to the proximal extremity where they are connected into the instrumentation 91 which is provided the capabilities for supplying electrical signals to the transducer and to receive electrical signals from the ultrasonic transducer 96.

Operation and use of the catheter 81 in connection with performing an ablation in the myocardium 106 may now be briefly described as follows. Assuming that it has been established that it is desired to perform an ablation in the myocardium, the ablation catheter is introduced into the heart in a conventional manner. When it is in the heart during mapping procedures, the echoes which are returned and picked up by the transducer 96 are observed on the screen 92. By watching the screen, it is easy to determine when the tip 86 is in contact with the wall of the heart, as for example the myocardium of the heart. When it has been determined that the ablation catheter 81 is in the desired position, radiofrequency energy can be supplied to the tip 86 to cause ablation of the myocardium 106 to occur. This ablation is depicted by a lesion 107 formed in the myocardium forward of the tip 86, which lesion can be increased in size by the continued application of RF energy to create a lesion of larger size, as for example 108 represented by the broken lines. Utilizing the ablation catheter of the present invention, it is possible to ascertain the depth of the lesion created by observing the screen 92. Since the propagation properties of ultrasound in tissue in the myocardium are well known, it is relatively easy utilizing conventional computer technology to convert echo time to depth. This is true because the transition from the lesion 107 to the tissue in the myocardium is highly echogenic, making it readily possible to ascertain this depth and to thereby precisely monitor the depth as ablation is occurring so that a lesion of the desired depth can be created.

Thus it can be seen that with the catheter 81 of the present invention, it is possible to ascertain when the tip 86 is in contact with the endocardium of the myocardium, and then to determine the depth of the lesion being made and to be able to stop ablation when the appropriate depth for the lesion has been reached. By way of example, the catheter 81 in utilizing the present method may be utilized for ablating accessory pathways to overcome the Wolf-Parkinson-White syndrome. Typically, these accessory pathways are usually on the epicardium rather than the endocardium between the junction of the atrium and the ventricle. The ultrasonic information which is generated may also be very helpful in ascertaining whether or not the tip 86 is close to a valve leaflet which helps to ensure that the ablation is being carried out in the optimal location.

In addition, the ablation catheter 81 should be very useful in diagnosing ventricular tachycardia, where an infarct area is present. Such infarct areas typically becomes fibrous and have a border which is very echogenic just over the layer of the infarct. Thus, prior to an ablation, the catheter could be utilized to determine where the viable myocardium is compared to the infarct area. In this way it is possible to diagnose the size and shape of the infarct.

It is apparent from the foregoing that there has been provided an endocardial mapping and ablation system in which a separately controlled steerable ablation catheter having the ultrasonic capabilities can be utilized for visualizing the arms of the catheter probe and also to ensure that any ablation which takes place, takes place in a proper portion of the wall of the wall forming the chamber of the heart. The ablation catheter also can be used to recognize when it is in close proximity to the wall of the heart and to what depth a lesion is being created.

What is claimed is:

1. A system for use in endocardial mapping and ablation, for introduction into a chamber of the heart formed by a wall and having a passage leading thereto comprising a catheter probe having a distal extremity adapted to be positioned in the chamber of the heart, a plurality of flexible longitudinally extending circumferentially spaced-apart arms adapted to be disposed within the chamber of the heart, electrodes carried by the arms and adapted to be moved into engagement with the wall of the heart, ultrasonically visible markers carried by the arms for encoding the arms so that one arm can be distinguished from another, an ablation catheter carried by and slidably mounted in the catheter probe and having a distal extremity movable into the chamber of the heart while the catheter probe is disposed therein, said ablation catheter having control means whereby the distal extremity can be moved independently of movement of the catheter probe while the distal extremity of the catheter probe is in the chamber of the heart, an ablation electrode carried by the distal extremity of the ablation catheter, ultrasonic viewing means carried by the distal extremity of the ablation catheter, said control means including means coupled to the distal extremity of the ablation catheter for moving the distal extremity of the ablation catheter into position to view the ultrasonically visible markers carried by the arms of the catheter probe, and said ultrasonic viewing means for identifying the arms and for ascertaining spacing of the arms, and means for creating an isochronal map of potentials being mapped within the chamber of the heart and means for correcting the isochronal map in accordance with the spacing in between the arms of the catheter probe.

2. A system as in claim 1 wherein said ultrasonic viewing means is disposed in close proximity to the ablation electrode so that when the ablation electrode is moved into contact with the wall of the heart to form an ablation, the area to be ablated can be viewed ultrasonically.

3. A system as in claim 2 wherein said ultrasonic viewing means comprises a transducer disposed in the ablation electrode and insulated therefrom and facing forwardly therefrom to propagate ultrasonic energy in a forward direction.

4. A system as in claim 2 wherein the ablation catheter has a longitudinal axis and wherein the ultrasonic viewing means includes means for directing ultrasonic energy in a direction at right angles to the longitudinal axis of the ablation catheter.

5. A method for endocardial mapping and ablation of the wall of a heart forming a chamber in the heart and having a passage leading thereto comprising steps of using a catheter probe having a plurality of longitudinally extending circumferentially spaced-apart flexible arms with electrodes carried thereby and having ultrasonically visible markers carried by the arms encoding the arms, and an ablation catheter having a distal extremity with ultrasonic viewing capabilities carried by the distal extremity further comprising the steps of introducing the catheter probe into the chamber of the heart and expanding the arms so that the electrodes carried thereby are moved into engagement with the wall forming the chamber of the heart, measuring potentials picked up by the electrodes, advancing the ablation catheter into the same chamber of the heart while the catheter probe is disposed therein, viewing the arms with ultrasonic energy by the ablation catheter to view the ultrasonic markers carried by the arms to ascertain the identity of the arms and to ascertain the spacing between the arms and performing an ablation in the wall of the heart with the ablation catheter.

6. A method as in claim 5 together with a step of creating an isochronal map of the potentials measured by the electrodes in contact with the wall forming the chamber and revising the isochronal map in accordance with the spacing between the arms.

7. A method as in claim 5 together with a step of advancing the ablation catheter so that an ablation electrode carried thereby is in engagement with the wall of the heart and viewing ultrasonically the portion of the wall engaged by the electrode to ascertain whether or not the ablation electrode is located appropriately to perform the desired ablation.

* * * * *

UNITED STATES PATENT AND TRADEMARK OFFICE
CERTIFICATE OF CORRECTION

PATENT NO. : 5,409,000
DATED : April 25, 1995
INVENTOR(S) : Mir A. Imran

It is certified that error appears in the above-indentified patent and that said Letters Patent is hereby corrected as shown below:

Col. 6, line 29, after "provided" insert --with--

Col. 7, line 57, after "catheter" insert --and said ultrasonic viewing means--

Col. 8, line 1, after "probe" delete ", and said ultrasonic viewing"

Col. 8, line 2, delete "means"

Col. 8, line 2, after "ascertaining" insert --the--

Col. 8, line 3, after "arms," delete "and"

Signed and Sealed this

Twenty-fifth Day of June, 1996

Attest:

BRUCE LEHMAN

Attesting Officer     Commissioner of Patents and Trademarks